Figure 1:
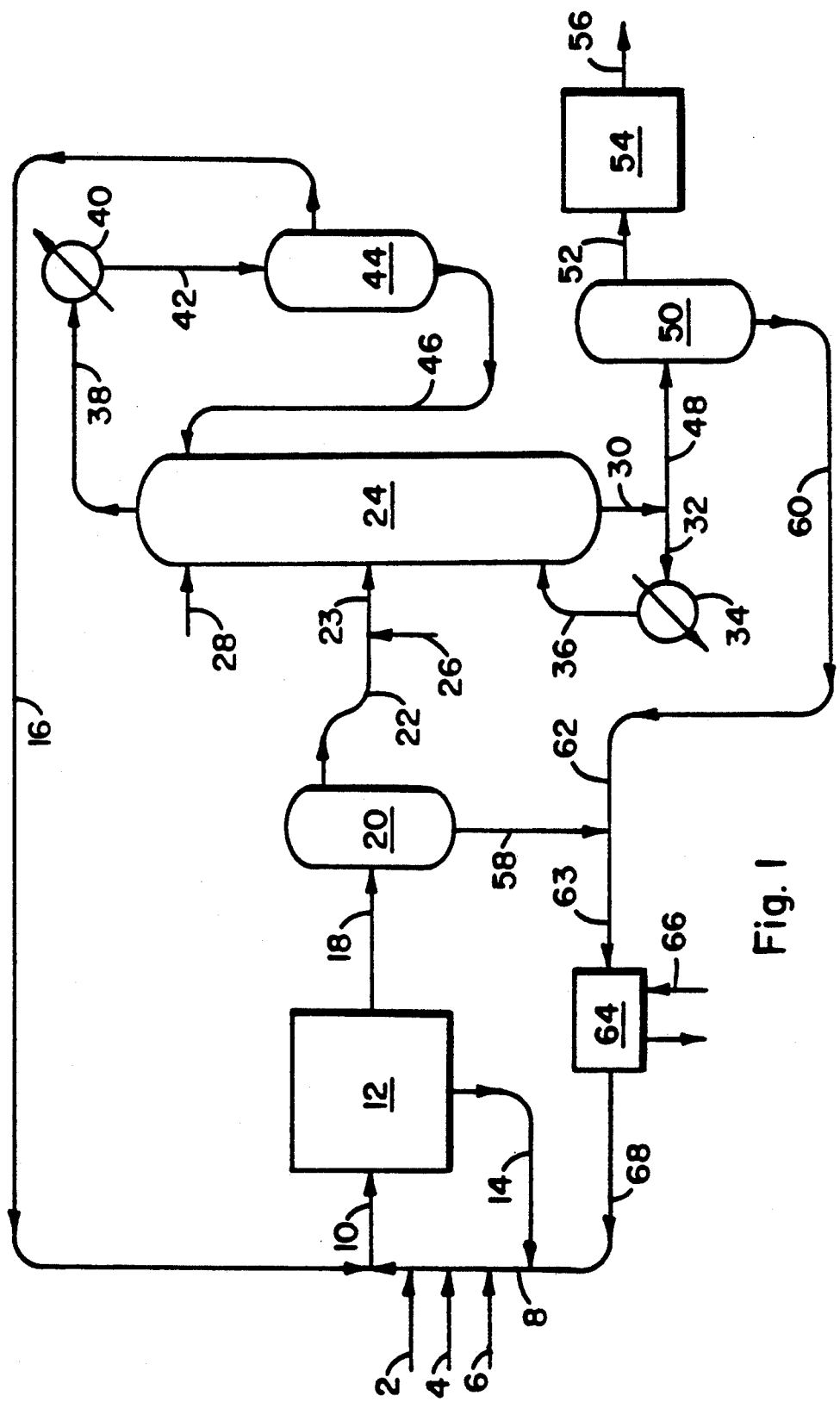

US005235118A

United States Patent [19]
Morris et al.

[11] Patent Number: 5,235,118
[45] Date of Patent: Aug. 10, 1993

[54] CONTINUOUS PROCESS FOR THE PREPARATION OF 2-ETHYL-2-(HYDROXYMETHYL)HEXANAL AND 2-BUTYL-2-ETHYL-1, 3-PROPANEDIOL

[75] Inventors: Don L. Morris; William A. Beavers; William E. Choate, all of Longview, Tex.

[73] Assignee: Eastman Kodak Company, Rochester, N.Y.

[21] Appl. No.: 937,039

[22] Filed: Aug. 31, 1992

Related U.S. Application Data

[62] Division of Ser. No. 886,917, May 22, 1992, which is a division of Ser. No. 735,575, Jul. 25, 1991, Pat. No. 5,146,004.

[51] Int. Cl.$^5$ .................... C07C 27/04; C07C 29/14; C07C 31/18
[52] U.S. Cl. .................... 568/862; 568/462; 568/463; 568/852; 568/861; 568/863
[58] Field of Search .............. 568/463, 462, 862, 863, 568/861, 852

[56] References Cited

U.S. PATENT DOCUMENTS
| | | | |
|---|---|---|---|
| 4,097,540 | 6/1978 | Immel et al. | 568/862 |
| 4,393,251 | 6/1983 | Broecker et al. | 568/862 |
| 5,118,883 | 6/1992 | Gehrer et al. | 568/862 |

FOREIGN PATENT DOCUMENTS
576087  3/1946  United Kingdom ............ 568/862

Primary Examiner—Werren B. Lone
Attorney, Agent, or Firm—J. Frederick Thomsen; William P. Heath, Jr.

[57] ABSTRACT

Disclosed is a continuous process for the manufacture of 2-ethyl-2-(hydroxymethyl)hexanal wherein 2-ethylhexanal, formaldehyde and a tertiary amine are continuously fed to a reaction zone and crude product comprising an aqueous phase and an organic phase containing 2-ethyl-2-(hydroxymethyl)hexanal and 2-ethylhexanal is continuously removed from the reaction zone Also disclosed are processes for (1) the azeotropic distillation of the organic phase of the crude product whereby unreacted 2-ethylhexanal is recovered and (2) the catalytic hydrogenation of the refined, organic phase of the crude product to produce 2-butyl-2-ethyl-1,3-propanediol.

6 Claims, 1 Drawing Sheet

CONTINUOUS PROCESS FOR THE PREPARATION OF 2-ETHYL-2-(HYDROXYMETHYL)HEXANAL AND 2-BUTYL-2-ETHYL-1, 3-PROPANEDIOL

This is a divisional application of copending application Ser. No. 07/886,917 filed May 22, 1992, which is a divisional of Ser. No. 07/735,575 filed Jul. 25, 1991, U.S. Pat. No. 5,146,004.

This invention pertains to an improved process for the preparation of 2-ethyl-2-(hydroxymethyl)hexanal by the condensation of 2-ethylhexanal and formaldehyde in the presence of a trialkylamine catalyst. More specifically, this invention pertains to a continuous process for the manufacture of 2-ethyl-2-(hydroxymethyl)-hexanal wherein 2-ethylhexanal, formaldehyde and a tertiary amine are continuously fed to a reaction zone, crude product comprising an aqueous phase and an organic phase containing 2-ethyl-2-(hydroxymethyl)-hexanal and 2-ethylhexanal is continuously removed from the reaction zone. This invention also concerns the azeotropic distillation of the organic phase of the crude product whereby unreacted 2-ethylhexanal is recovered. Finally, this invention provides for the catalytic hydrogenation of the refined, organic phase of the crude product to produce 2-butyl-2-ethyl-1,3-propanediol.

Japanese Patent Publication 73-43,085 describes the preparation of 2-ethyl-2-(hydroxymethyl)hexanal (EHMH) by the reaction of 2-ethylhexanal and formaldehyde in the presence of alkali metal hydroxides at a pH of 8.0 to 11.0. The EHMH is converted to 2-butyl-2-ethyl-1,3-propanediol (BEPD) by the Cannizzaro reaction using a second equivalent of formaldehyde and alkali metal hydroxide. This process generates one equivalent of sodium formate for each equivalent of BEPD. Purification of the aqueous sodium formate stream or disposal of this stream is the major disadvantage of this process. Another disadvantage is the added raw material cost occasioned by the use of an extra equivalent of formaldehyde to convert the BHMH to BEPD. British Patent 1,320,387 discloses the preparation of 2-ethyl-2-(hydroxymethyl)hexanal by heating with vigorous agitation a mixture of 2-ethylhexanal, formaldehyde and triethylamine at 90°–93° C. for eight hours. A slight stoichiometric excess of formaldehyde was used and the amount of triethylamine employed was 4.6 weight percent based on the total weight of the materials. Despite the eight-hour reaction time and vigorous agitation of the batch reaction mixture, the percent conversion of 2-ethylhexanal reported was approximately 81.2. Thus, the product obtained contained a substantial amount of unreacted formaldehyde which can detrimentally affect the performance of catalysts, especially nickel catalysts, used to hydrogenate EHMH to BEPD. The presence of such substantial amounts of formaldehyde also is undesirable due to the formation of formaldehyde polymers which can foul or plug processing equipment such as piping used to transport effluents from distillation columns.

We have found that 2-ethyl-2-(hydroxymethyl)hexanal may be produced at improved rates by reacting aqueous formaldehyde with a stoichiometric excess of 2-ethylhexanal in the presence of a tertiary amine wherein the tertiary amine functions both as a catalyst and a co-solvent. Thus, one embodiment of the present invention is a continuous process for the preparation of 2-ethyl-(hydroxymethyl)hexanal by the condensation of 2-ethylhexanal and formaldehyde in the presence of a tertiary amine by the steps comprising:

(1) continuously feeding to a reaction zone 2-ethylhexanal, aqueous formaldehyde and a tertiary amine, wherein (i) a stoichiometric excess of 2-ethylhexanal is fed and (ii) the feed rates of tertiary amine and 2-ethyl-hexanal maintain in the reaction zone a tertiary amine:2-ethylhexanal weight ratio of at least 0.2; and (2) continuously removing from the reaction zone a crude product mixture comprising (i) an aqueous phase and (ii) an organic phase containing 2-ethyl-2-(hydroxymethyl)hexanal and 2-ethylhexanal.

We have found that when the weight ratio of tertiary amine:2-ethylhexanal is maintained at a value of at least 0.2, the tertiary amine functions both as a catalyst for the condensation reaction and as a co-solvent for the 2-ethylhexanal and the aqueous formaldehyde, thereby permitting more intimate contact of the reactants and an improved reaction rate. British Patent 1,320,387 referred to above proposes the use of alkanols and cyclic ethers as solubilizers to improve mixing and accelerate the reaction We have found that the use of methanol in the process gives little improvement in reaction rate Furthermore, the use of the proposed extraneous materials presents recovery and recycle problems including toxicological and environmental considerations. The use of alkanols or cyclic ethers also can be detrimental to the efficient separation of the aqueous and organic phases recovered from the reaction zone.

The 2-ethylhexanal is fed to the reaction zone in a stoichiometric excess relative to the formaldehyde fed. Generally, the 2-ethylhexanal excess is at least 0.1 mole percent, preferably about 0.3 to 0.6 mole excess relative to the stoichiometric amount. The aqueous formaldehyde solution used in our novel process may contain from about 20 to 80 weight percent formaldehyde and a minor amount, e.g., up to 1 weight percent, of methanol as a stabilizer. The aqueous formaldehyde preferably contains about 30 to 50 weight percent formaldehyde.

The tertiary amine catalyst/co-solvent preferably is a trialkyl amine having a total carbon content of up to about 12 such as trimethylamine, triethylamine, tripropylamine and the like. As stated above, the tertiary amine and 2-ethylhexanal are fed to the reaction zone at rates which maintain a tertiary amine:2-hexanal weight ratio of at least 0.2 in the reaction zone. Although the weight ratio of tertiary amine:2-ethylhexanal may be as high as about 0.5, we have found that good production rates may be achieved by maintaining the ratio in the range of about 0.3 to 0.4.

The condensation reaction may be carried out at a temperature of about 90° to 140° C. and a pressure of about 1 to 10 bars absolute. Preferred reaction conditions are a temperature of about 100° to 125° C. and a pressure of about 1 to 3 bars absolute.

The practice of the condensation process provided by the present invention permits the preparation of EHMH at improved production rates even though the degree of agitation which may be achieved in continuous operation typically is substantially less than the agitation which is possible when operating a batch process. The formation of by-products such as 2-ethylhexanol, formate salts, and high molecular weight esters resulting from the Tischenko reaction of EHMH is minimized. Normally, the production rate (the space-time yield) is at least 100 grams EHMH per liter hour wherein liter refers to the total volume (in liters) of the mixture in the reaction zone. At space-time yields of 100 g/L-hour, the process typically gives a formaldehyde conversion of at least 90 mole percent which results in the organic phase of the crude reaction product having a formaldehyde content of less than 1.7 weight percent based on the weight of the organic phase. It is preferred to operate the process in a manner to achieve space time yields of EHMH in the range of about 100 to 500 g/L hour while obtaining a formaldehyde conversion of greater than about 90 to 95 mole percent and a formaldehyde concentration of less than 1.7 weight percent in the organic phase of the crude product.

The continuous condensation process may be carried out by continuously feeding 2-ethylhexanal, aqueous formaldehyde and a tertiary amine, including recycle 2-ethylhexanal and tertiary amine, to a reaction zone and continuously removing a crude product stream comprising an aqueous phase and an organic phase. The reaction zone may comprise one or more reactors designed to provide agitation of the reaction mixture, e.g., reactors equipped with agitators, a tube reactor containing packing material, recirculating reactors and the like. To obtain formaldehyde conversions of at least 90 mole percent, the residence time in the reaction zone typically is about 3.5 to 6 hours. The effluent from the reaction zone is fed to a decanter wherein all, or a substantial portion of, the aqueous phase is separated from the organic phase which contains EHMH product, tertiary amine, unreacted 2-ethylhexanal, BEPD and minor amounts of formaldehyde, the ammonium formate salt of the tertiary amine, methanol and higher molecular weight organics such as formaldehyde condensation products and C-17 and C-18 esters [2-ethylhexanoate and 2-ethyl-2-(hydroxymethyl)hexanoate esters of 2-butyl-2-ethyl-1,3-propanediol]. The aqueous phase contains the ammonium formate salt of the tertiary amine which may be recovered by treating the aqueous phase with an alkali metal hydroxide. For example, the aqueous phase may be contacted with sodium hydroxide to produce sodium formate and the tertiary amine which is recovered from the resulting mixture by distillation.

In a second embodiment of the present invention, the crude organic phase obtained in accordance with the condensation process described hereinabove is fed continuously to an extractive, azeotropic distillation zone to recover the tertiary amine and unreacted 2-ethylhexanal. This embodiment of our invention provides a continuous process for the recovery of 2-ethylhexanal and tertiary amine from a mixture comprising 2-ethyl-2-(hydroxymethyl)hexanal, 2-ethylhexanal, tertiary amine and water by the steps of:

(1) continuously feeding the mixture to the mid section of a distillation column;
(2) continuously feeding water to the middle or upper section of the distillation column;
(3) continuously removing from the distillation column a vapor stream comprising 2-ethylhexanal, tertiary amine and water;
(4) condensing the vapor stream of step (3) to obtain a two phase liquid and separating the organic phase rich in 2-ethylhexanal and tertiary amine; and
(5) continuously removing from the lower section of the distillation column a two phase mixture depleted in 2-ethylhexanal and tertiary amine.

The extractive, azeotropic distillation zone comprises a distillation column and decanters for separation of the aqueous and organic effluents of the distillation column.

The crude organic phase obtained from the condensation process is fed continuously to the midsection of the distillation column. Water also is fed to the distillation at or near the top and/or to the mid-section of the column. The distillation column is operated at approximately atmospheric pressure, a base temperature of about 100° to 110° C. and a head temperature of about 96° to 98° C. to minimize decomposition of the EHMH and formation of esters via the Tischenko reaction. Maintaining the column head temperature at about 96° to 98° C. maximizes the amount of 2-ethylhexanal removed as vapor from the distillation column.

A vapor stream comprising tertiary amine and a constant boiling mixture (binary azeotrope) consisting of 48.4 weight percent 2-ethylhexanal and 51.6 weight percent water and having a boiling point of 96.4° C. is removed continuously at or near the top of the column. The vapor stream is condensed and the organic phase comprising 2-ethylhexanal and tertiary amine is separated, e.g., by means of a decanter, from the resulting two-phase liquid and recycled to the condensation reaction zone. The aqueous phase of the two-phase liquid may be recycled to the upper portion of the distillation column.

A liquid stream comprised of all, or essentially all, of the EHMH fed to the distillation column, water, BEPD and minor amounts of formaldehyde, 2-ethylhexanal, and C-17 and C-18 esters is removed continuously from the base of the distillation column and fed to a decanter wherein the aqueous and organic phases of the column underflow are separated. The aqueous phase of the underflow stream containing minor amounts of the formate salt of the tertiary amine and EHMH may be treated with an alkali metal hydroxide to recover the tertiary amine for recycle to the condensation reaction zone. The organic phases comprises a major amount of EHMH and minor amounts of water, formaldehyde, 2-ethylhexanal, and C-17 and C-18 esters. The refined organic phase obtained from the extractive, azeotropic distillation zone preferably is comprised of at least 80 weight percent EHMH and less than about 2 weight percent formaldehyde.

In another embodiment of the present invention, the refined organic phase is fed continuously to a hydrogenation zone wherein the EHMH component of the refined organic phase is catalytically hydrogenated at elevated temperatures and pressures, according to known means, to produce BEPD. For example, the catalysts and/or processes described in U.S. Pat. Nos. 4,097,540, 4,181,810, 4,250,337, 4,386,219, 4,393,251, 4,851,592 and 4,855,515 may be used to convert the EHMH to BEPD. This embodiment involves a process for the preparation of BEPD by the condensation and recovery processes described hereinabove in combination the hydrogenation of the EHMH to BEPD. Thus, our invention includes a process for the continuous preparation of 2-butyl-2-ethyl-1,3-propanediol which comprises the steps of:

(1) continuously feeding to a reaction zone 2-ethylhexanal, aqueous formaldehyde and a tertiary amine, wherein (i) a stoichiometric excess of 2-ethylhexanal is fed and (ii) the feed rates of tertiary amine and 2-ethylhexanal maintain in the reaction zone a tertiary amine:2-ethylhexanal weight ratio of at least 0.2;
(2) continuously removing from the reaction zone a crude product mixture comprising (i) an aqueous phase and (ii) an organic phase containing 2-ethyl-2-

(hydroxymethyl)hexanal, 2-ethylhexanal and tertiary amine;
(3) continuously feeding the organic phase of step (2) to the mid section of a distillation column;
(4) continuously feeding water to the middle or upper section of the distillation column;
(5) continuously removing from the distillation column a vapor stream comprising 2-ethylhexanal, tertiary amine and water;
(6) condensing the vapor stream of step (5) to obtain a two-phase liquid, separating the organic phase rich in 2-ethylhexanal and tertiary amine, and recycling the organic phase to the reaction zone;
(7) continuously removing from the lower section of the distillation column a two-phase mixture depleted in 2-ethylhexanal and tertiary amine;
(8) continuously separating the two-phase mixture of step (5) into (i) an aqueous phase and (ii) an organic phase rich in 2-ethyl-2-(hydroxymethyl) hexanal; and
(9) continuously feeding the organic phase of step (8) to a hydrogenation zone wherein the 2-ethyl-2-(hydroxymethyl)hexanal is hydrogenated to 2-butyl-2-ethyl-1,3-propanediol in the presence of a hydrogenation catalyst.

The hydrogenation zone comprises a pressure vessel containing one or more fixed beds of a suitable hydrogenation catalyst. The product of the hydrogenation zone may be recycled to dissipate the heat of hydrogenation.

The hydrogenation preferably is carried out by passing the refined organic phase over one or more fixed beds of a supported nickel catalyst at a total pressure of about 21 to 36 bars absolute and at a hydrogenation zone exit temperature of about 150° to 170° C. The catalyst may comprise nickel deposited on a catalyst support material such as silica, alumina, carbon, titanium dioxide, molecular sieves, zeolites, kieselguhr, etc. Normally, the supported nickel catalysts are comprised of about 1 to 90 weight percent nickel, calculated as [Ni], based on the total weight of the catalyst. Preferred nickel catalysts comprise about 1 to 70 weight percent nickel on silica/alumina.

The conversion of EHMH to BEPD in the hydrogenation zone typically is greater than 99%, e.g., 99.7% or greater. The product of the hydrogenation zone normally comprises at least 75 weight percent BEPD and minor amounts of water, methanol, 2-ethylhexanol, BEPD 2-ethylhexanoate and BEPD 2-ethyl-2-(hydroxymethyl)hexanoate. We have found that the activity of the nickel hydrogenation catalyst does not decline measurably over 60 days of continuous operation.

The hydrogenation product may be refined according to known purification techniques to obtain BEPD having a purity of 99.5% or greater. Thus, the effluent from the hydrogenation vessel may be fed to a flash pot wherein the pressure is reduced and essentially all of the material, except for any high boiling components present, is flashed to the mid section of a first distillation column operated at about 200° C. under reduced pressure. Low boiling components comprising water and 2-ethylhexanol are removed from the top of the column and remainder is removed from the base of the column and fed to the mid section of a second distillation column, also operated at 200° C. and at reduced pressure. The ester impurities are underflowed from the second column and purified BEPD, typically containing less than 50 ppm nitrogen, is removed from the top of the column.

The accompanying Figure is a process flow diagram illustrating a system embodying the principles of the processes of the present invention. It is, of course, possible that the processes may be operated by modifying the specific processes illustrated by the Figure.

Referring to the Figure, fresh 2-ethylhexanal, aqueous formaldehyde and tertiary amine are fed continuously by means of conduits 2, 4, 6, 8, and 10 to condensation reaction zone 12 along with reaction mixture recycle, fed via conduits 14, 8 and 10, and recycle 2-ethylhexanal and tertiary amine, fed via conduits 16 and 10. The 2-ethylhexanal:formaldehyde mole ratio fed by conduit 10 normally is in the range of about 1.1:1 to about 1.6:1. The residence time of the reaction mixture within zone 12 is about 3.5 to 6 hours. Crude product comprising (i) an aqueous phase and (ii) an organic phase containing 2-ethyl-2-(hydroxymethyl)hexanal and 2-ethylhexanal is removed continuously from reaction zone 12 and transported by conduit 18 to decanter 20.

The crude organic phase comprising EHMH, 2-ethylhexanal and tertiary amine is transported by conduits 22 and 23 from decanter 20 to the mid section of extractive, azeotropic distillation column 24. Fresh water is supplied to column 24 by conduits 26 and 23 as a mixture with the crude organic phase and/or by conduit 28. Alternatively, a portion or all of the fresh water may be provided to column 24 by means of conduit 28. The base of column 24 is maintained at about 100° to 110° C. by recirculating a liquid phase from the base of column 24 through lines 30 and 32, reboiler 34 and line 36. Vapor comprising water, 2-ethylhexanal and tertiary amine is removed continuously from column 24 via conduit 38, condensed in condenser 40 and fed by conduit 42 to decanter 44. The temperature of the vapor phase exiting column 24 normally is in the range of about 96° to 98° C. The organic phase comprising 2-ethylhexanal and tertiary amine is recycled via conduits 16 and 10 to reaction zone 12. The aqueous phase is returned to the upper portion of distillation column 24 by conduit 46.

A liquid phase comprising all, or essentially all, of the EHMH fed to distillation column 24, water and minor amounts of formaldehyde, 2-ethylhexanal, and 2-ethylhexanoate and 2-ethyl-2-(hydroxymethyl)hexanoate esters of 2-butyl-2-ethyl-1,3-propanediol is removed continuously from the base of column 24 by conduit 30 and fed via conduit 48 to decanter 50. The refined organic phase separated in decanter 50 is fed via conduit 52 to hydrogenation zone 54 wherein the EHMH is catalytically hydrogenated to BEPD as described hereinabove. The hydrogenation zone may comprise one or more pressure vessels containing a supported hydrogenation catalyst. The hydrogenation preferably is carried out at a temperature of about 150° to 170° C. and a pressure of about 28 to 36 bars absolute in the presence of a supported nickel catalyst, e.g., about 50 weight percent nickel on alumina.

An important feature of the present invention is the provision of the EHMH containing, refined organic phase which contains less than (i) 2.0 weight percent formaldehyde and (ii) 1.0 weight percent 2-ethylhexanal. The upper limits of formaldehyde and 2-ethylhexanal preferably are 3.0 and 5.0 weight percent, respectively. The low formaldehyde concentration permits the use of nickel catalysts and relatively low hydrogenation pressures in hydrogenation zone 54. Nickel hydrogenation catalysts normally are rapidly deactivated by the presence of significant amounts of formaldehyde, e.g., formaldehyde concentrations of about 3.0 weight percent or higher, in hydrogenation feed mixtures. The low concentrations of 2-ethylhexanal results in the production of BEPD at high yields e.g., 85% or greater, based on the 2-ethylhexanal fed to reaction zone 12.

Hydrogenation product is removed continuously from hydrogenation zone 54 through conduit 56 and transported to a BEPD refining zone (not shown) comprising a distillation train wherein high and low boilers are separated from the BEPD according to conventional purification techniques. The refined BEPD thus obtained typically has a purity of 99.5% or greater and a nitrogen content of less than 50 ppm.

The aqueous phases, containing the formate salt of the tertiary amine, collected in decanters 20 and 54 are combined by means of conduits 58, 60 and 62 and fed via conduit 63 to amine recovery zone 64. The tertiary amine is liberated from the formate salt of the amine by treating the aqueous phases with an alkali metal hydroxide, supplied via line 66, and the tertiary amine thus recovered is returned to reaction zone 12 by conduits 68, 8 and 10. An aqueous waste stream containing alkali metal formate is removed from amine recovery zone 64 for disposal in a conventional waste water treatment plant.

The processes provided by the present invention are further illustrated by the following examples.

EXAMPLES 1-3 AND COMPARATIVE EXAMPLES 1 AND 2

A one liter Parr autoclave was charged with 2-ethylhexanal (334 g, 406 mL, 2.6 mole), 44% aqueous formaldehyde (136.4 g, 122 mL, 2.0 mole) and varying amounts of triethylamine to determine the effect of increasing triethylamine concentration on reaction rate. After purging with nitrogen, the autoclave was sealed and heated at 100° C. for one hour. The autoclave was cooled and the contents were analyzed for formaldehyde (HCHO) by calorimetric analysis and for 2-ethyl-2-(hydroxymethyl)hexanal (EHMH) by gas chromatography analysis. The yield of EHMH was calculated based on the 2-ethylhexanal consumed which was determined after correcting the gas chromatograph area for methanol and excess 2-ethylhexanal. Table I sets forth the amount of triethylamine (TEA, g/mL), the concentration by weight of triethylamine based on the total weight of the materials charged (TEA, %), the mole percent of formaldehyde converted (HCHO Conv.) and the percent yield of EHMH obtained.

TABLE I

| Example | TEA g/mL | TEA % | HCHO Conv. | Yield EHMH |
|---|---|---|---|---|
| 1 | 47.0/65.4 | 10 | 86 | 68.2 |
| 2 | 70.6/98.0 | 15 | 92 | 83.4 |
| 3 | 94.0/130.6 | 20 | 95 | 88.0 |
| C-1 | 9.4/13.0 | 2 | 40 | 35.2 |
| C-2 | 23.6/32.6 | 5 | 74 | 48.9 |

The data presented in Table I establish the beneficial effects obtained by the use of larger amount of triethylamine. The weight ratios of the triethylamine to 2-ethylhexanal initially fed in these batch experiments vary from the ratios resulting from continuous operation wherein the triethylamine and reactants are continuously consumed.

EXAMPLES 4-6 AND COMPARATIVE EXAMPLES 3 AND 4

To determine the effect of carrying out the condensation reaction in the presence of methanol as a co-solvent, Examples 1-3 and Comparative Examples 1 and 2 were repeated except that the reactions were carried out in the presence of 30 weight percent methanol based on the total weight of materials charged to the autoclave. The amounts of methanol used (MeOH, g) in each example and the triethylamine concentration, the formaldehyde conversion and yield of EHMH, as described in the preceding examples, are set forth in Table II.

TABLE II

| Example | TEA % | MeOH | HCHO Conv. | Yield EHMH |
|---|---|---|---|---|
| 4 | 10 | 156 | 81.0 | 81.3 |
| 5 | 15 | 162 | 84.0 | 87.0 |
| 6 | 20 | 170 | 90.0 | 85.0 |
| C-3 | 2 | 144 | 72.8 | 65.0 |
| C-4 | 5 | 148 | 78.8 | 72.8 |

The results reported in Table II establish that the presence of methanol improves formaldehyde conversion and yield of 2-ethyl-2-(hydroxymethyl)hexanal when used in combination with low concentrations of triethylamine. However, superior results are achieved only when triethylamine is used in initial concentrations of 10 to 20 weight percent.

EXAMPLE 7

This example illustrates the continuous operation of the processes of our invention employing the production system depicted in the Figure. All parts given are by weight unless stated otherwise.

Fresh 2-ethylhexanal, 44% aqueous formaldehyde and triethylamine are fed at 406.0, 271.0 and 1.66 parts per hour, respectively, to reaction zone 12 via conduits 2, 4, 6, 8 and 10 along with 257.0 parts per hour 2-ethylhexanal, 1.4 parts per hour formaldehyde and 132.9 parts per hour triethylamine supplied by recycle conduits 16 and 68. Reaction zone 12 comprises a plurality of recirculating reactors maintained at about 110° C. and about 4.5 bars absolute. The residence time of the reaction mixture in the reaction zone is about 3.7 hours. Crude condensation reaction mixture comprising EHMH is removed continuously from reaction zone 12 at a rate of 1085.0 parts per hour and fed to decanter 20 wherein the crude organic phase is separated from the aqueous phase. The space time yield of EHMH averages 117 g/liter hour.

Crude organic phase is removed from decanter 20 at a rate of 920.3 parts per hour and fed to distillation column 24 via lines 22 and 23 along with water which is added at 150.0 parts per hour through conduit 26. No water is fed through conduit 28. The base of column 24 is maintained at about 105° C., as described hereinabove, to produce an overhead vapor stream which is removed continuously via conduit 38, condensed in condenser 40 and fed by conduit 42 to decanter 44. The organic phase from decanter 44 comprising 2-ethylhexanal and tertiary amine is recycled via conduits 16 and 10 to reaction zone 12 at the rate of 364.0 parts per hour. The aqueous phase from decanter 44 is returned to the upper portion of column 24 by conduit 46.

A liquid phase stream is removed continuously from column 24 and transported by conduits 30 and 48 to decanter 50 at a rate of 692.5 parts per hour. The refined organic phase separated in decanter 50 is fed via conduit 52 at 541.7 parts per hour to hydrogenation zone 54 wherein the EHMH is catalytically hydrogenated to BEPD using a 50% nickel on alumina catalyst. The hydrogenation is carried out in the liquid phase at a pressure of 35.5 bars absolute and a catalyst bed exit temperature of 160° C. using a trickle bed reactor. Hydrogenation zone 54 included means for recycling effluent from the hydrogenation reactor to the reactor feed at a volume ratio of 10 parts effluent per part fresh feed.

The hydrogenation product of conduit 56 is flash distilled at 50 torr to remove most of the high boiling impurities. The top takeoff of the flash column is fed to a second column which removes all low boiling impurities. This column is operated at 6.5 bars absolute with a base temperature of 200° C. The base overflow from this column is fed to the refining column This column is operated at 20 torr with a base temperature of 210° C. BEPD of 99.7 percent purity is removed from the top of the column and a small amount of high boiling esters is removed from the base of the column.

The yield of BEPD is 85 percent based on the 2-ethylhexanal, and 68 percent based on the formaldehyde, fed to the reaction zone 12. Utilization of the triethylamine catalyst is very efficient with an average usage of 1 part by weight triethylamine per 200 parts by weight BEPD.

The compositions, by weight percent, of the mixtures present in conduits 10, 16, 18, 22, 23, 42, 48, 52 and 56 during the operation of the processes described in Example 4 are set forth in Table III wherein HCHO is formaldehyde, HEH is 2-ethylhexanal, TEA is triethylamine, EHMH is 2-ethyl-2-(hydroxymethyl) hexanal, Esters are 2-ethylhexanoate and 2-ethyl-2-(hydroxymethyl)hexanoate esters of 2 butyl 2-ethyl-1,3-propanediol and BEPD is 2-butyl-2-ethyl-1,3-propanediol. These mixtures also contain varying amounts of additional components such as methanol, ethanol, TEA formate and formaldehyde condensation products, depending on the particular mixture.

TABLE III

| Conduit | Water | HCHO | HEH | TEA | EHMH | Esters | BEPD | Other |
|---|---|---|---|---|---|---|---|---|
| 10 | 14.0 | 2.2 | 34.5 | 12.4 | 28.5 | 1.9 | 3.4 | 3.1 |
| 16 | 1.9 | 0.4 | 70.3 | 24.0 | 1.9 | — | — | 1.5 |
| 18 | 13.7 | 0.8 | 23.7 | 8.1 | 33.2 | 2.9 | 6.7 | 10.9 |
| 22 | 2.7 | 0.9 | 27.9 | 9.5 | 39.1 | 3.4 | 7.9 | 8.6 |
| 23 | 16.4 | 0.7 | 24.0 | 8.2 | 33.6 | 2.9 | 6.8 | 7.4 |
| 42 | 49.5 | 0.1 | 22.4 | 10.7 | 0.7 | — | — | 16.6 |
| 48 | 22.9 | 0.9 | 1.2 | 0.2 | 50.8 | 5.6 | 10.6 | 7.8 |
| 52 | 8.2 | 1.1 | 1.5 | 0.3 | 65.0 | 7.2 | 13.5 | 3.2 |
| 56 | 8.1 | — | Trace | Trace | — | 7.1 | 78.6 | 6.2 |

The invention has been described in detail with particular reference to preferred embodiments thereof, but it will be understood that variations and modification can be effected within the spirit and scope of the invention.

We claim:

1. A continuous process for the preparation of 2-butyl-2-ethyl-1,3-propanediol which comprises the steps of:
   (1) continuously feeding to a reaction zone 2-ethylhexanal, aqueous formaldehyde and a tertiary amine, wherein (i) a stoichiometric excess of 2-ethylhexanal is fed and (ii) the feed rates of tertiary amine and 2-ethylhexanal maintain in the reaction zone a tertiary amine:2-ethylhexanal weight ratio of at least 0.2;
   (2) continuously removing from the reaction zone a crude product mixture comprising (i) an aqueous phase and (ii) an organic phase containing 2-ethyl-2-(hydroxymethyl)hexanal, 2-ethylhexanal and tertiary amine;
   (3) continuously feeding the organic phase of step (2) to the mid-section of a distillation column;
   (4) continuously feeding water to the middle or upper section of the distillation column;
   (5) continuously removing from the distillation column a vapor stream comprising 2-ethylhexanal, tertiary amine and water;
   (6) condensing the vapor stream of step (5) to obtain a two-phase liquid, separating the organic phase rich in 2-ethylhexanal and tertiary amine, and recycling the organic phase to the reaction zone;
   (7) continuously removing from the lower section of the distillation column a two-phase mixture depleted in 2-ethylhexanal and tertiary amine;
   (8) continuously separating the two-phase mixture of step (5) into (i) an aqueous phase and (ii) an organic phase rich in 2-ethyl-2-(hydroxymethyl)hexanal; and
   (9) continuously feeding the organic phase of step (8) to a hydrogenation zone wherein the 2-ethyl-2-(hydroxymethyl)hexanal is contacted with a supported nickel hydrogenation catalyst at a total pressure of about 21 to 36 bars absolute and at a hydrogenation zone exit temperature of about 150° to 170° C. to produce 2-butyl-2-ethyl-1,3-propanediol.

2. Process according to claim 1 wherein the tertiary amine is a trialkylamine containing up to about 12 carbon atoms and the reaction zone is maintained at a temperature of about 100° to 125° C. and a pressure of about 1 to 3 bars absolute.

3. A continuous process for the preparation of 2-butyl-2-ethyl-1,3-propanediol which comprises the steps of:
   (1) continuously feeding to a reaction zone 2-ethylhexanal, aqueous formaldehyde and a tertiary amine, wherein (i) the mole ratio of 2-ethylhexanal to formaldehyde fed to the reaction zone is about 1.1:1 to 1.6:1 and (ii) the feed rates of tertiary amine and 2-ethylhexanal maintain in the reaction zone a tertiary amine:2-ethylhexanal weight ratio of about 0.2 to 0.5;
   (2) continuously removing from the reaction zone a crude product mixture comprising (i) an aqueous phase and (ii) an organic phase containing 2-ethyl-2-(hydroxymethyl)hexanal and 2-ethylhexanal; whereby the formaldehyde concentration of organic phase (2) (ii) is less than about 1.7 weight percent an the space-time yield of 2-ethyl-2-(hydroxymethyl)hexanal is at least 100 g per liter-hour;

(3) continuously feeding the organic phase of step (2) to the mid-section of a distillation column;

(4) continuously feeding water to the middle or upper section of the distillation column;

(5) continuously removing from the distillation column a vapor stream comprising 2-ethylhexanal, tertiary amine and water;

(6) condensing the vapor stream of step (5) to obtain a two-phase liquid, separating the organic phase rich in 2-ethylhexanal and tertiary amine, and recycling the organic phase to the reaction zone;

(7) continuously removing from the lower section of the distillation column a two-phase mixture depleted in 2-ethylhexanal and tertiary amine;

(8) continuously separating the two-phase mixture of step (5) into (i) an aqueous phase and (ii) an organic phase rich in 2-ethyl-2-(hydroxymethyl)hexanal; and (9) continuously feeding the organic phase of step (8) to a hydrogenation zone wherein the 2-ethyl-2-(hydroxymethyl)hexanal is contacted with a supported nickel hydrogenation catalyst at a total pressure of about 21 to 36 bars absolute and at a hydrogenation zone exit temperature of about 150° to 170° C. to produce 2-butyl-2-ethyl-1,3-propanediol.

4. Process according to claim 3 wherein the base of the distillation column is maintained at a temperature of about 100° to 110° C. and the tertiary amine is a trialkylamine having up to about 12 carbon atoms.

5. A continuous process for the preparation of 2-butyl-2-ethyl-1,3-propanediol which comprises the steps of:

(1) continuously feeding to a reaction zone 2-ethylhexanal, aqueous formaldehyde and a tertiary amine selected from triethylamine and tripropylamine, wherein (i) the mole ratio of 2-ethylhexanal to formaldehyde fed to the reaction zone is about 1.1:1 to 1.6:1 and (ii) the feed rates of tertiary amine and 2-ethylhexanal maintain int he reaction zone a tertiary amine:2-ethylhexanal weight ratio of about 0.2 to 0.5;

(2) continuously removing from the reaction zone a crude product mixture comprising (i) an aqueous phase and (ii) an organic phase containing 2-ethyl-2-(hydroxymethyl)hexanal and 2-ethylhexanal; whereby the formaldehyde concentration of organic phase (2) (ii) is less than about 1.7 weight percent an the space-time yield of 2-ethyl-2-(hydroxymethyl)hexanal is at least 100 g per liter-hour;

(3) continuously feeding the organic phase of step (2) to the mid-section of a distillation column wherein the base of the distillation column is maintained at a temperature of about 100° to 110° C.;

(4) continuously feeding water to the middle or upper section of the distillation column;

(5) continuously removing from the distillation column a vapor stream comprising 2-ethylhexanal, tertiary amine and water;

(6) condensing the vapor stream of step (5) to obtain a two-phase liquid, separating the organic phase rich in 2-ethylhexanal and tertiary amine, and recycling the organic phase to the reaction zone;

(7) continuously removing from the lower section of the distillation column a two-phase mixture depleted in 2-ethylhexanal and tertiary amine;

(8) continuously separating the two-phase mixture of step (5) into (i) an aqueous phase and (ii) an organic phase rich in 2-ethyl-2-(hydroxymethyl)hexanal; and (9) continuously feeding the organic phase of step (8) to a hydrogenation zone wherein the 2-ethyl-2-(hydroxymethyl)hexanal is contacted with a supported nickel hydrogenation.

6. Process according to claim 5 wherein the supported nickel hydrogenation catalyst comprises about 1 to 70 weight percent nickel on silica/alumina.

* * * * *

UNITED STATES PATENT AND TRADEMARK OFFICE
CERTIFICATE OF CORRECTION

PATENT NO. : 5,235,118
DATED : August 10, 1993
INVENTOR(S) : Don L. Morris et al.

It is certified that error appears in the above-identified patent and that said Letters Patent is hereby corrected as shown below:

Column 11, line 1 (Claim 3, line 18), "an" should be --- and ---.

Column 12, line 11 (Claim 5, line 19), "an" should be --- and ---.

Column 12, line 37 (Claim 5, line 45), between "hydrogenation" and the period (.), --- catalyst at a total pressure of about 21 to 36 bars absolute and at a hydrogenation zone exit temperature of about 150 to 170° to produce 2-butyl-2-ethyl-1,3-propanediol --- should be added.

Signed and Sealed this

Fifth Day of April, 1994

Attest:

*Attesting Officer*

BRUCE LEHMAN

*Commissioner of Patents and Trademarks*